United States Patent [19]
Dumont et al.

[11] Patent Number: 6,022,306
[45] Date of Patent: Feb. 8, 2000

[54] METHOD AND APPARATUS FOR COLLECTING HYPERCONCENTRATED PLATELETS

[75] Inventors: Larry Joe Dumont, Arvada; Linda A. Taylor, Littleton, both of Colo.; Geert Van Waeg, Brussels, Belgium

[73] Assignee: COBE Laboratories, Inc., Lakewood, Colo.

[21] Appl. No.: 08/924,787

[22] Filed: Sep. 5, 1997

Related U.S. Application Data

[60] Continuation-in-part of application No. 08/672,089, Jun. 27, 1996, Pat. No. 5,722,926, which is a division of application No. 08/423,578, Apr. 18, 1995, Pat. No. 5,674,173.

[51] Int. Cl.[7] .................................................. B01B 1/00
[52] U.S. Cl. ........................... 494/10; 494/37; 494/45; 604/6; 424/532
[58] Field of Search .................... 494/3, 5, 10, 37, 494/43, 45, 56, 57; 210/782, 786, 787; 435/2; 604/6; 424/532

[56] References Cited

U.S. PATENT DOCUMENTS

| | | |
|---|---|---|
| 1,684,870 | 9/1928 | Lewis . |
| 2,616,619 | 11/1952 | MacLeod . |
| 2,878,995 | 3/1959 | Dega . |
| 3,771,715 | 11/1973 | Baram . |
| 3,823,869 | 7/1974 | Loison . |
| 3,825,175 | 7/1974 | Sartory . |
| 4,091,989 | 5/1978 | Schlutz . |
| 4,146,172 | 3/1979 | Cullis et al. . |
| 4,187,979 | 2/1980 | Cullis et al. . |
| 4,268,393 | 5/1981 | Persidsky et al. . |
| 4,269,718 | 5/1981 | Persidsky . |
| 4,322,298 | 3/1982 | Persidsky . |
| 4,350,283 | 9/1982 | Leonian . |
| 4,386,730 | 6/1983 | Mulzet ........................... 494/43 |
| 4,387,848 | 6/1983 | Kellog et al. ......... 494/43 ......... Ito . |

(List continued on next page.)

FOREIGN PATENT DOCUMENTS

| | | |
|---|---|---|
| 0 406 485 A1 | 1/1991 | European Pat. Off. . |
| 0 408 462 A2 | 1/1991 | European Pat. Off. . |
| 0 419 346 A2 | 3/1991 | European Pat. Off. . |
| 2545283 | 4/1977 | Germany . |
| 2918834 | 11/1980 | Germany . |
| 3700122 | 7/1988 | Germany . |
| 37 00 122 | 7/1998 | Germany . |
| 55-045437 | 3/1980 | Japan . |
| 55-045452 | 3/1980 | Japan . |
| WO 85/02561 | 6/1985 | WIPO . |
| WO 94/02157 | 2/1994 | WIPO . |
| WO 94/27698 | 12/1994 | WIPO . |

OTHER PUBLICATIONS

Maxim D. Persidsky et al., "Separation of Platelet–Rich Plasma by Modified Centrifugal Elutriation", Journal of Clinical Apheresis, 1:18–24 (1982).

John F. Jemionek et al., "Special Techniques for the Separation of hemopoietic Cells", Current Methodology in Experimental Hematology, 1984, pp. 12–16.

Nancy M. Heddle et al., "The Role of the Plasma From Platelet Concentrates in Transfusion Reactions", The New England Journal of Medicine, vol. 331, No. 10, Sep. 8, 1994, pp. 625–628, 670 and 671.

(List continued on next page.)

*Primary Examiner*—Tony G. Soohoo
*Attorney, Agent, or Firm*—Edie O'Connor; Bruce R. Winsor

[57] ABSTRACT

The instant invention relates to a method and the apparatus for collecting a hyperconcentrated platelet product. A fluid containing platelets and other particles flows into a fluid chamber at a flow rate. The flow rate of the fluid is selected to retain the majority of the platelets in the fluid chamber in a saturated bed. The platelets are collected from the fluid chamber without collecting the other particles to form a hyperconcentrated other particle reduced platelet product.

43 Claims, 5 Drawing Sheets

U.S. PATENT DOCUMENTS

| | | |
|---|---|---|
| 4,416,654 | 11/1983 | Schoendorfer et al. . |
| 4,425,112 | 1/1984 | |
| 4,464,167 | 8/1984 | Schoendorfer et al. . |
| 4,675,117 | 6/1987 | Neumann et al. . |
| 4,701,267 | 10/1987 | Watanabe et al. . |
| 4,708,710 | 11/1987 | Dunn, Jr. . |
| 4,708,712 | 11/1987 | Mulzet . |
| 4,798,579 | 1/1989 | Penhasi . |
| 4,808,151 | 2/1989 | Dunn, Jr. et al. . |
| 4,834,890 | 5/1989 | Brown et al. ............................. 494/45 |
| 4,846,974 | 7/1989 | Kelley et al. . |
| 4,885,137 | 12/1989 | Lork . |
| 4,933,291 | 6/1990 | Daiss et al. . |
| 4,936,998 | 6/1990 | Nishimura et al. . |
| 4,939,081 | 7/1990 | Figdor et al. . |
| 4,939,087 | 7/1990 | Van Wie et al. . |
| 5,076,911 | 12/1991 | Brown et al. ............................. 494/10 |
| 5,078,671 | 1/1992 | Dennehey et al. . |
| 5,089,146 | 2/1992 | Carmen et al. . |
| 5,203,999 | 4/1993 | Hugues . |
| 5,213,970 | 5/1993 | Lopez-Berestein . |
| 5,229,012 | 7/1993 | Pall et al. . |
| 5,282,982 | 2/1994 | Wells . |
| 5,298,171 | 3/1994 | Biesel . |
| 5,316,666 | 5/1994 | Brown et al. . |
| 5,316,667 | 5/1994 | Brown et al. . |
| 5,360,542 | 11/1994 | Williamson, IV . |
| 5,362,291 | 11/1994 | Williamson, IV . |
| 5,370,802 | 12/1994 | Brown . |
| 5,397,479 | 3/1995 | Kass et al. . |
| 5,403,272 | 4/1995 | Deniega et al. . |
| 5,409,813 | 4/1995 | Schwartz . |
| 5,501,795 | 3/1996 | Pall et al. . |

OTHER PUBLICATIONS

Bernard J. Van Wie et al., "The Effect of Hematocrit and Recycle on Cell Separations", Plasma Ther. Transfus. Technol., 1986, 7:373–388.

Bernard J. Van Wie, Conceptualization and Evaluation of Techniques for Centrifugal Separation of Blood Cells: Optimum Process Conditions, Recycle and Stagewase Processing, Dissertation, 1982, pp. 27–58.

A. Tulp et al., "A Separation Chamber to Sort Cells and Cell Organelles by Weak Physical Forces V.V. Sector–Shaped Chamber and Its Application to the Separation of Peripheral Blood Cells", Journal of Immunological Methods 69 (1984), pp. 281–295.

Carl G. Figdor et al., Theory and Practice of Centrifugal Elutriation (CE) Factors Influencing the Separation of Human Blood Cells, Cell Biophysics 5, 105–118 (1983).

P.C. Keng et al., "Characterization of the Separation Properties of the Beckman Elutriator System", Cell Biophysics 3 (1981), pp. 41–56.

Claes F. Hogman, Leukocyte Depletion of Blood Components, 1994, pp. 1, 156–173.

A.S. Buchanan et al., "Principle of a Counter–streaming Centrifuge for the Separation of Particles of Different Sizes", Nature, Apr. 24, 1948, pp. 648–649.

"Cost–Effectivenes of Leukocyte Depletion of Blood Components", presented at the 1993 AABB Meeting, Miami Beach, FL.

I. Sniecinski, "Prevention of Immunologic and Infectious Complications of Transfusion by Leukocyte Depletion", Prevention of Complications of Transfusion, Chapter 18, pp. 202–211. No Date.

G. Stack et al,. "Cytokine Generation in Stored Platelet Concentrates", Transfusion, 1994, 34:20–25.

H. Brandwein et al., Asahi Sepacell PL10A Leukocyte Removal Filter: Efficiency with Random Donor Platelet Pool, PALL Technical Report. No Date.

J. Whitbread et al., Performance Evaluation of the Sepacell PL10A Filter and PALL PXL 8 Filter: Measurement of Leukocyte Residuals and Consistency, PALL Technical Report. No Date.

R. Brown et al., "Evaluation of a new Separation method Utilizing Plasma Recirculation and Autoelutriation", Transfusion, 1994, vol. 34, Supp.

Richard J. Sanderson et al., "Design Principles for a Counterflow Centrifugation Cell Separation Chamber", Analytical Biochemistry 71, 615–622 (1976).

Harvey J. Brandwein et al., "Asahi Depacell PL–10A Leukocyte Removal Filter Description and Review of Claims", PALL Technical Report. No date.

Judy H. Angelbeck, Adverse Reactions to Platelet Transfusion, Risks and Probable Causes, pp. 1–14. No Date.

Beckman, "Centrifugal Elutriation", pp. 4–7. No Date.

LRF6/LRF10, High Efficiecny Leukocyte Removal Filter Systems for Platelets PALL Biomedical Products Corporation. No Date.

J.F. Jemionek, "Variations in CCE Protocol for Cell Isolation", Elutriation, pp. 17–41. No Date.

English Language abstract of DE 3734170. Oct. 1987.

Multi Chamber Counterflow Centrifugation System, Dijkstra Vereenigde B.V., 6 pgs. No Date.

Nancy Besso et al Asahi Sepcel PL–10A Leukocyte Removal Filler: Effect of Post–Filtration Flush with Saline, PALL Techical Report. No Date.

Sanderson, Richard J., "Separation of Different Kinds of Nucleated Cells from Blood by Centrifugal Elutriation", Cell Esparation: Methods and Selected Applications, vol. 1, 1982, pp. 153–168.

Robert Grabske, "Separating Cell Populations by Elutriation", pp. 1–8. No Date.

P.E. Lindahl, "On Counter Streaming Centrifugation in the Separation of Cells and Cell Fragments", pp. 411–415. No Date.

C. Almici et al., "Counterflow Centrifugal Elutriation: Present and Future", Bone Marrow Transplatation, 19993, 12: 105–109.

J. Freedman et al., White Cell Depletion Of Red Cell And Pooled Random–Donor Platelet Concentrates By Filtration And Residual Lymphocyte Subset Analysis, Transfusion, 1991, vol. 31, No. 5, pp. 433–440.

A. Bruil et al., Asymmetric Membrane Filters For The Removal Of Leukocytes From Blood, Journal of Biomed. Materials Research, vol. 25, 1459–1480, 1991.

Sunny Dzik, Leukodepletion Blood Filters: Filter Design And Mechanisms Of Leukocyte Removal, Transfusion Medicine Reviews, vol. VII, No. 2, Apr. 1993, pp. 65–77.

P.D. Drumheller et al., The Effects Of RPM And Recycle On Separation Efficiency In A Clinical Blood Cell Centrifuge, Journal of Biomechanical Engineering, Nov. 1987, vol. 109, pp. 324–329.

R.J.Oxford et al., Monitoring And Automated Optimization Of A Cell Centrifuge, IEEE/Eighth Annual Conference of the Engineering in Medicine and Biology Society, pp. 925–927.

R.J. Oxford et al., Interface Dynamics In A Centrifugal Cell Separator, Transfusion, Nov.–Dec., 1988, vol. 28, No. 6 pp. 588–592.

Benefits of Leukocyte Filtration for Red Cell and Platelet Blood Procuts, Transfusion Associated CMV, 1994 pp. 1–18,.

N.M. Heddle et al., A Prospective Study to Identify The Risk Factors Associated With Acute Reactions To Platelet And Red Cell Transfusions; Transusion, 1993; 33:794–797.

Designed to provide the Reliabilty and Performance to Harvest a High Yield Component Product, The Haemonetics V50 Apheresis System. No Date.

Haemonetics Mobile Collection System Owner's Operating and Maintenance Manual, 1991, pp. 3–2 through 3–7 and pp. 1–6.

E. A. Burgstaler et al., White Blood Cell Contamination of Apheresis Platelets Collected on the COBE Spectra, COBE Blood Component Technology. No Date.

T.H. Price et al., Platelet Collection Using the COBE Spectra, COBE Blood Component Technology,1989.

"Lower is Better!", (flyer) PALL Biomedical Products Company, 1991.

AS 104 Cell Separator, Fresenius No Date.

CS–3000 Blood Cell Separator, Powerful Technology, Fenwal Laboratories, No Date.

The Mobile Collection System Gives You Easier Access to More Donors Than Ever Before, Haemonetics. No Date.

J. Whitbread et al., Reduction of C3A Fragment Levels Following Leukodepletion Using a PALL PXL8 Filter. No Date.

T.A. Takahshi et al., Bradykinin Formation in a Platelet Concentrate Filtered with a Leukocyle–removal Filter Made of Nonwoven Polyester Fibers with a Negatively Charged Surface. No Date.

CS–3000 Plus Blood Cell Separator, Baxter, No Date.

Brief Operating Instructions, Fresenius MT AS 104 blood cell separator, (OP), pp. 1–1 to 7.33. No Date.

English language abstract of SU 1725117 A,1989.

English language abstract of SU 1255136,1984.

English language abstract of SU 1236366,1984.

English language abstract of SU 1091071,1982.

CS–3000 Plus Blood Cell Separator Operators's Manual, Baxter, No Date.

METHOD AND APPARATUS FOR COLLECTING HYPERCONCENTRATED PLATELETS

RELATED APPLICATIONS

This application is a continuation-in-part of application Ser. No. 08/672,089 to Hlavinka et al. filed Jun. 27, 1996 now U.S. Pat. No. 5,722,926 which is a divisional application of Ser. No. 08/423,578 filed Apr. 18, 1995 now U.S. Pat. No. 5,674,173.

BACKGROUND OF THE INVENTION

Field of the Invention

The present invention relates to an apparatus and method for collecting high concentration leukocyte-reduced platelets. Leuko-reduced, high concentration or hyperconcentrated platelets are those that have concentrations >$2.1 \times 10^6$/$\mu$L with less than $1 \times 10^6$ total white blood cells per 50–60 mL volume of collection or per transfusion dose. The invention has particular advantages for collecting high concentrated or hyperconcentrated (HC) platelets for transfusion to babies in utero.

DESCRIPTION OF THE RELATED ART

It is sometimes desirable to have a source of hyperconcentrated platelets for transfusion purposes. A condition called fetomaternal allioimmune thrombocytopenia (FMAIT), for example, may exist where a mother is making antibodies against her baby's platelets in utero. This is due to a difference in antigens between the mother's and baby's platelets and occurs at a frequency of 1 birth per 1,000–2,000 births. In such a situation it is frequently desirable to transfuse hyperconcentrated platelets to the baby in the womb to prevent intracranial hemorrhage on the part of the baby. Such therapeutic options include the administration of weekly fetal platelet transfusions during the later part of the pregnancy. A one time transfusion could also be used as needed.

Hyperconcentrated platelets are also needed and used for pediatric transfusions and for platelet storage wherein the platelets are stored with additive preservative solution.

Platelet concentrations are prepared by apheresis of suitable donors. In the case of FMAIT one suitable donor may be the mother herself. For a weekly platelet transfusion regimen for FMAIT it is desirable the post transfusion platelet count be between 300 and $500 \times 10^9$/L. Calculation of the volume of platelet concentrate required to produce the desired post-transfusion platelet count is based on the formula:

$$\text{Volume} = \frac{P_1 V_{FP} R}{P_c}$$

where $P_1$=platelet increment $V_{FP}$=feto-placental blood volume, and $P_c$=platelet count of concentrate R=factor.

From this it can be seen that the greater the platelet count of the concentrate, the less volume of platelet concentrate needs to be transfused. Therefore it is desirable to have a hyperconcentrate or high concentration of platelets to reduce the volume needed to be transfused in utero. Such a reduced volume can then result in a reduced procedure time and further minimize the inherent risks of such an in utero procedure.

Similar advantages of a hyperconcentrate exist for pediatric transfusion. Also a hyperconcentrate product is better for those cases where storage solution dilutes the end platelet product.

As noted above, a hyperconcentrate of platelets is achieved through apheresis of suitable donors including potentially, the patient's mother.

In platelet transfusion situations donated whole blood is processed generally by centrifugation to separate or remove platelets and these collected platelets are then infused into the patient. However, if a patient receives an excessive number of foreign white blood cells with the platelets, the patient may run the risk of receiving a transmittable infection.

Centrifugation is a process of separating lighter portions of a suspension from heavier portions by centrifugal force. During centrifugation the centrifuge rotates a blood reservoir to separate components within the reservoir by the centrifugal force. In use, blood enters the reservoir while it is rotating at a very rapid speed and centrifugal force stratifies the blood components.

Centrifuges are effective at separating platelets from whole blood, however they typically are unable to separate all of the white blood cells from the platelets. Prior art blood separation and centrifugation devices are typically unable to consistently (99% of the time) produce platelet product that meets the "leukopoor" or "leuko-reduced" standard of less than $1 \times 10^6$ white blood cells per transfusion dose of platelets.

Because typical centrifuge platelet collection processes are unable to consistently and satisfactorily separate white blood cells from platelets, other processes have been added after the initial separation of platelets. In one procedure, after centrifuging, platelets are passed through a porous woven or non-woven media filter, which may have a modified surface, to remove white blood cells. Conventional porous filters however, may be inefficient because they may permanently remove or trap approximately 5–20% of the platelets. These conventional filters also reduce "platelet viability," as a percentage of the platelets cease to function properly after passage through a filter and such platelets may be partially or fully activated and are likely to clog the filter. Porous filters are also expensive and often require additional time consuming manual labor to perform a filtration process.

Another separation process is one known as centrifugal elutriation which separates cells suspended in a liquid medium without a membrane filter. Such separation is in accordance with the different sedimentation velocities of the particles.

One improved procedure for collecting leukopoor or leukocyte-reduced platelets is set forth in copending patent application U.S. application Ser. No. 08/423,578 to Hlavinka et al. filed Apr. 18, 1995, incorporated herein in its entirety by reference, now U.S. Pat. No. 5,674,173. This application describes apparatus and method for separating white blood cells from platelets by using a saturated bed to filter and obstruct the passage of white blood cells so that leukopoor platelets may be collected.

Previous methods to collect hyperconcentrated platelets include use of the COBE® Spectra™ two stage sealless blood component centrifuge manufactured by the assignee of the invention. However, such methods do not produce a sufficiently leukopoor product. Platelets with excessive number of foreign white cells can be rejected by the patient or the fetus and as noted above can present an overall harm instead of benefit.

A need existed therefore for apparatus and method to produce a leukopoor hyperconcentrated platelet product.

SUMMARY OF THE INVENTION

The present invention is directed to apparatus and method that substantially obviate the disadvantages of the above noted prior art methods and apparatus. To achieve these and other advantages and in accordance with the purposes of the invention, as embodied and broadly described herein, the invention comprises an apparatus for separating platelets from blood through centrifugation and for further separating white blood cells and other formed elements from the separated platelets. The apparatus further concentrates the separated platelets into a hyperconcentrated leukopoor platelet product for collection. The apparatus includes a motor and a centrifuge rotor coupled to the motor for rotation about an axis of rotation. A fluid chamber is also capable of being mounted on the rotor. Means are provided for separating blood components and for providing platelets to the fluid chamber. Means are provided for also controlling the platelet collect pump and the resulting collection of platelets in the fluid chamber to achieve the requisite hyperconcentrate leukopoor platelet product.

Another aspect of the invention relates to the method of collecting leukopoor hyperconcentrated platelets for later transfusion. The method includes controlling the collect pump for platelets and separating the platelets using a saturated bed to achieve the desired platelet yield. The method further varies the collect flow rate to remove the leuko-reduced platelets for collection.

Another aspect of the invention is to provide apparatus and method for collecting a hyperconcentrated leukopoor collection of platelets and a leukopoor regular concentration collection of platelets.

An additional aspect of the invention is to provide for a hyperconcentrated leukopoor collection of platelets that can be stored using existing techniques for later transfusion.

DESCRIPTION OF THE PREFERRED EMBODIMENTS

Reference will now be made in detail to the preferred embodiments of the invention illustrated in the accompanying drawings.

A preferred embodiment of the present invention is described by referring to its use with a COBE® SPECTRA™ two stage sealless blood component centrifuge manufactured by the assignee of the invention with an LRS® system described in greater detail in U.S. patent application Ser. No. 08/423,578 to Hlavinka et al. filed Apr. 18, 1995 incorporated herein by reference. The COBE® SPECTRA™ centrifuge incorporates a one-omega/two-omega sealless tubing connection as disclosed in U.S. Pat. No. 4,425,172 to Ito, the entire disclosure of which is incorporated herein by reference. The COBE® SPECTRA™ centrifuge also uses a two-stage blood component separation channel substantially as disclosed in U.S. Pat. No. 4,708,712 to Mulzet, the entire disclosure of which is also incorporated herein by reference. There was a need with the COBE® Spectra™ centrifuge to effectively collect leuko-reduced hyperconcentrate platelets. Although the preferred embodiment of the invention is described in combination with the COBE® SPECTRA™ centrifuge, this description is not intended to limit the invention in any sense.

As will be apparent to one having skill in the art, the present invention may be advantageously used in a variety of centrifuge devices commonly used to separate blood into its components. In particular, the present invention may be used with any centrifugal apparatus whether or not the apparatus employs a two stage channel or a one-omega/two-omega sealless tubing connection. The invention also may be used with centrifugal apparatus that uses a single stage channel such as set forth in U.S. patent application Ser. No. 08/853,374 to Hlavinka filed May 8, 1997 incorporated herein in its entirety by reference. Such a single stage separation channel can also be of a type substantially disclosed in U.S. Pat. No. 4,094,461 to Kellogg et al. and U.S. Pat. No. 4,647,279 to Mulzet et al., the entire disclosures of which are also incorporated by reference. It can also be any single stage separation channel used with apheresis apparatus.

The apparatus for collecting hyperconcentrated leukopoor platelets from a liquid comprises a centrifuge rotor coupled to a motor for rotating the centrifuge rotor about an axis of rotation. As embodied herein and illustrated in FIG. 1, centrifuge 10 includes a rotor 12. The rotor 12 has an annular groove or passageway 14 having an open upper surface adapted to receive a conduit or channel 44 of a tubing set 70 shown in FIG. 2. The passageway 14 completely surrounds the rotor's axis of rotation 13 and is bounded on an inner surface by wall 15 positioned on a top surface 17 of rotor 12. A motor 16 is coupled to rotor 12 to rotate the rotor 12 about the axis of rotation 13. This coupling is accomplished directly or indirectly through a shaft 18 connected to an arm 19 that mounts to the rotor 12. Alternately, the shaft 18 may be coupled to the motor 16 through a gearing transmission (not shown). A shroud 20 is positioned on the rotor 12 to protect the motor 16 and shaft 18.

Figure 1:
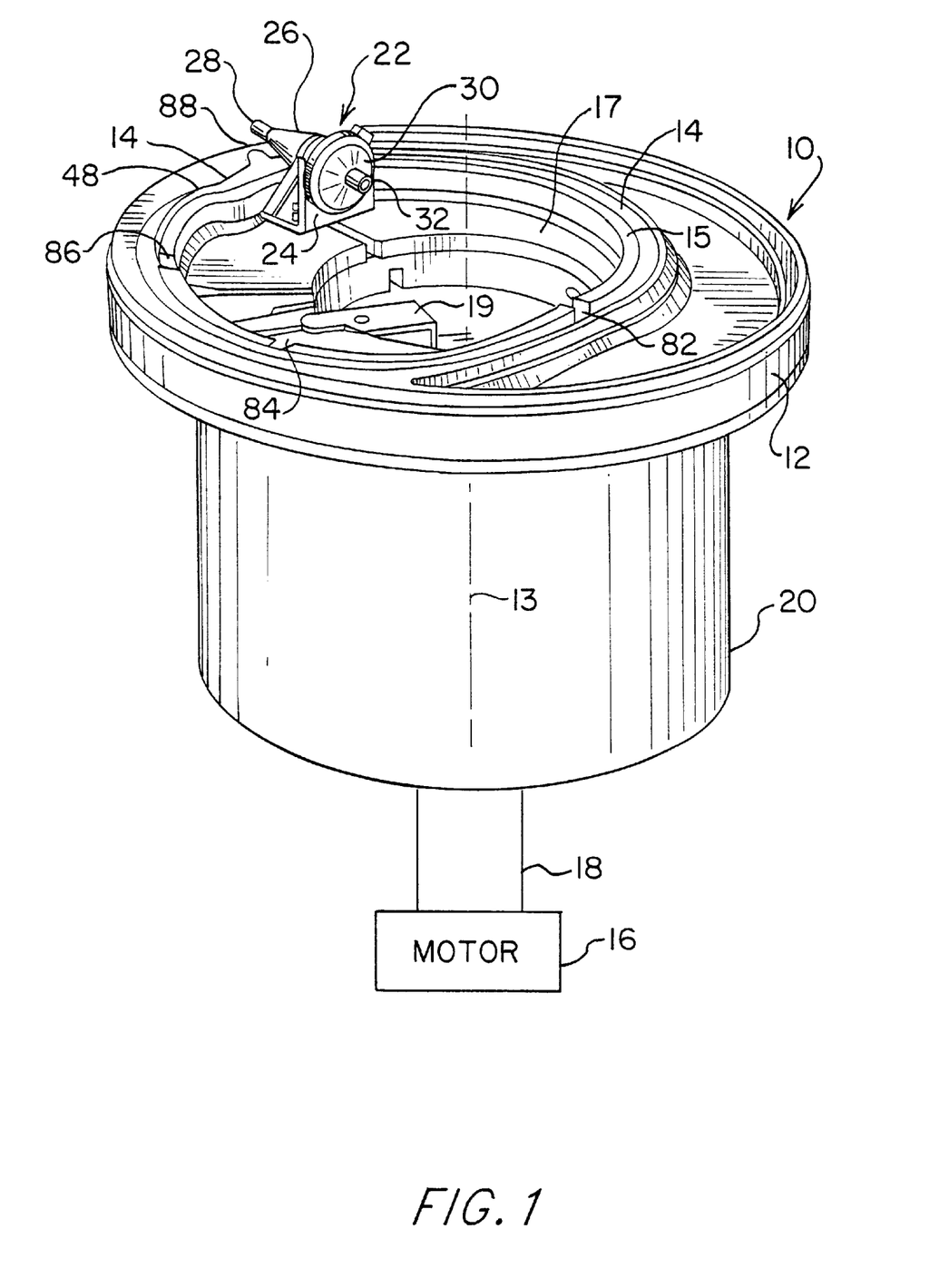
FIG. 1 is a perspective view of a centrifuge apparatus in accordance with a preferred embodiment of the invention.

A holder 24 is provided for holding a fluid chamber 22 on the rotor with an outlet of the fluid chamber positioned closer to the axis of rotation than an inlet of the fluid chamber. As embodied herein and as illustrated in FIG. 1, the holder may include a mounting bracket 24 for maintaining a fluid chamber 22 on rotor 12 with an outlet 32 generally positioned closer to the rotation axis 13 than an inlet 28. The fluid chamber 22 fits within the mounting bracket 24 as illustrated in FIG. 1. The fluid chamber 22 may also be secured to the rotor 12 at alternate locations, such as beneath passageway 14. The fluid chamber 22 may be constructed of a transparent or translucent copolyester plastic, such as PETG, if desired.

The fluid chamber is more particularly described in U.S. Pat. No. 5,674,173 to Hlavinka et al. incorporated herein by reference.

The volume of the fluid chamber 22 should be at least large enough to accommodate enough platelets to provide a saturated fluidized particle bed (described below) for a particular range of flow rates, particle sizes, and centrifuge rotor 12 speeds.

Figure 3:
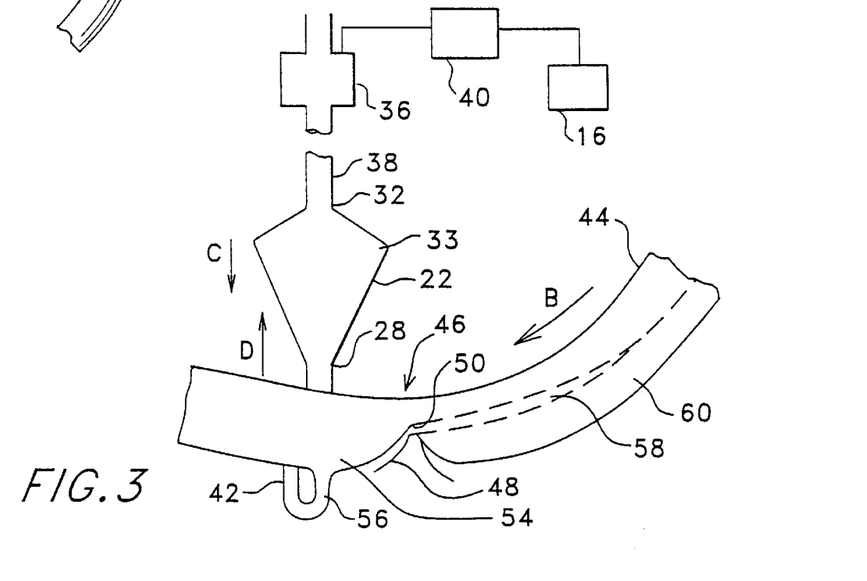
FIG. 3 is a partial schematic view of the apparatus of FIG. 1 illustrating a detailed view of components of the apparatus.

There is also provided means for supplying a substance to the inlet of the fluid chamber at a varying flow rate. As embodied herein and as schematically illustrated in FIG. 3, a collect pump 36 is fluidly connected to the fluid chamber 22 through outflow tubing 38. The collect pump 36 applies a vacuum force to the fluid chamber 22 or acts as a flow restrictor for drawing fluid and particles into the fluid chamber 22 through the inlet 28. The collect pump 36 is preferably a peristaltic pump or impeller pump configured to prevent significant damage to blood components, but any fluid pumping or drawing device may be provided. In an alternative embodiment (not shown), the collect pump 36 may be fluidly connected to the inlet of the fluid chamber 22 to directly move substances into and through the fluid chamber 22. The pump 36 may be mounted at any convenient location.

There are also provided means for controlling the motor and/or the supply means to maintain a saturated fluidized bed of platelets within the fluid chamber and to cause other particles such as white blood cells to be retained in the chamber. As embodied herein and illustrated in FIG. 3, the controlling means may include a controller 40 connected to both the centrifuge motor 16 and the pump 36. As explained in detail below, during a centrifuge operation, controller 40 maintains a saturated fluidized particle bed within the fluid chamber 22 to separate particles. Controller 40 may include a computer having programmed instructions provided by a ROM or RAM as is commonly known in the art.

In accordance with the instant invention the controller 40 regulates the collect pump 36 to vary the flow rate of the substance supplied to the fluid chamber 22 as is more fully described below. The controller may regulate the collect pump through various methods. For example, to control or regulate the pump, the controller 40 may vary the electricity, (i.e. voltage, current, frequency, time duration, etc.), provided to the pump 36. Alternatively the controller 40 may vary the flow rate to the chamber 22 by regulating a valving structure (not shown) positioned either within an inflow tubing 42 connected to the inlet 28 or within outflow tubing 38. The controller 40 may receive an input from a flow detector (not shown) positioned within the inflow tubing 42 to monitor the flow rate of substances entering the fluid chamber 22. The controller may also receive an input from a collect concentrate or flow monitor as more fully described below. Although a single controller 40 having multiple operations is schematically depicted in the embodiment shown in FIG. 3, the control means of the invention may include any number of individual controllers, each for performing a single function or a number of functions. The controller 40 may control flow rates in many other ways as is known in the art.

Figure 2:
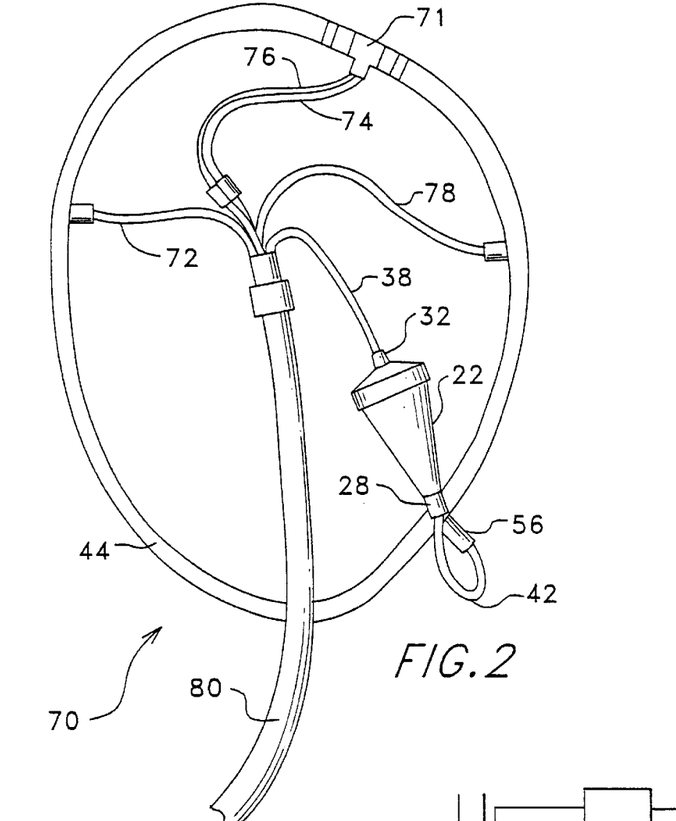
FIG. 2 depicts a portion of a tubing set in accordance with the invention.

As described above, the rotor 12 is configured with an annular passageway 14 that is open along a top surface as illustrated in FIG. 1. This passageway 14 is provided to receive a channel 44 of tubing set 70. As best illustrated in FIG. 2, tubing set 70 preferably includes a semi-rigid conduit formed into a channel 44 having a generally rectangular cross-section. A connector 71 joins ends of the channel 44 to form an annular or loop shape that fits within passageway 14. A supply line 78 provides whole blood to an inlet of the semi-rigid channel 44, while a tubing segment 42, outlet lines 72, 74, and a control line 76 allow for removal of blood components during a centrifuge operation and flow control within the channel 44. Further details of the general configuration and functioning of the channel 44, tubing segment 42, and lines 72, 74, 76 and 78 are described in U.S. Pat. No. 4,708,712.

A protective sheath 80 surrounds the lines 72, 74, 76, 78 and outflow tubing 38. When the channel 44 of the tubing set 70 is removably positioned within the passageway 14, the lines 72, 74, 76 and 78 extend through slots 82, 84, 86, respectively, formed in wall 15, while the inflow tubing 42 rests in a slot 88 formed by passageway 14 (FIG. 1).

Figure 4:
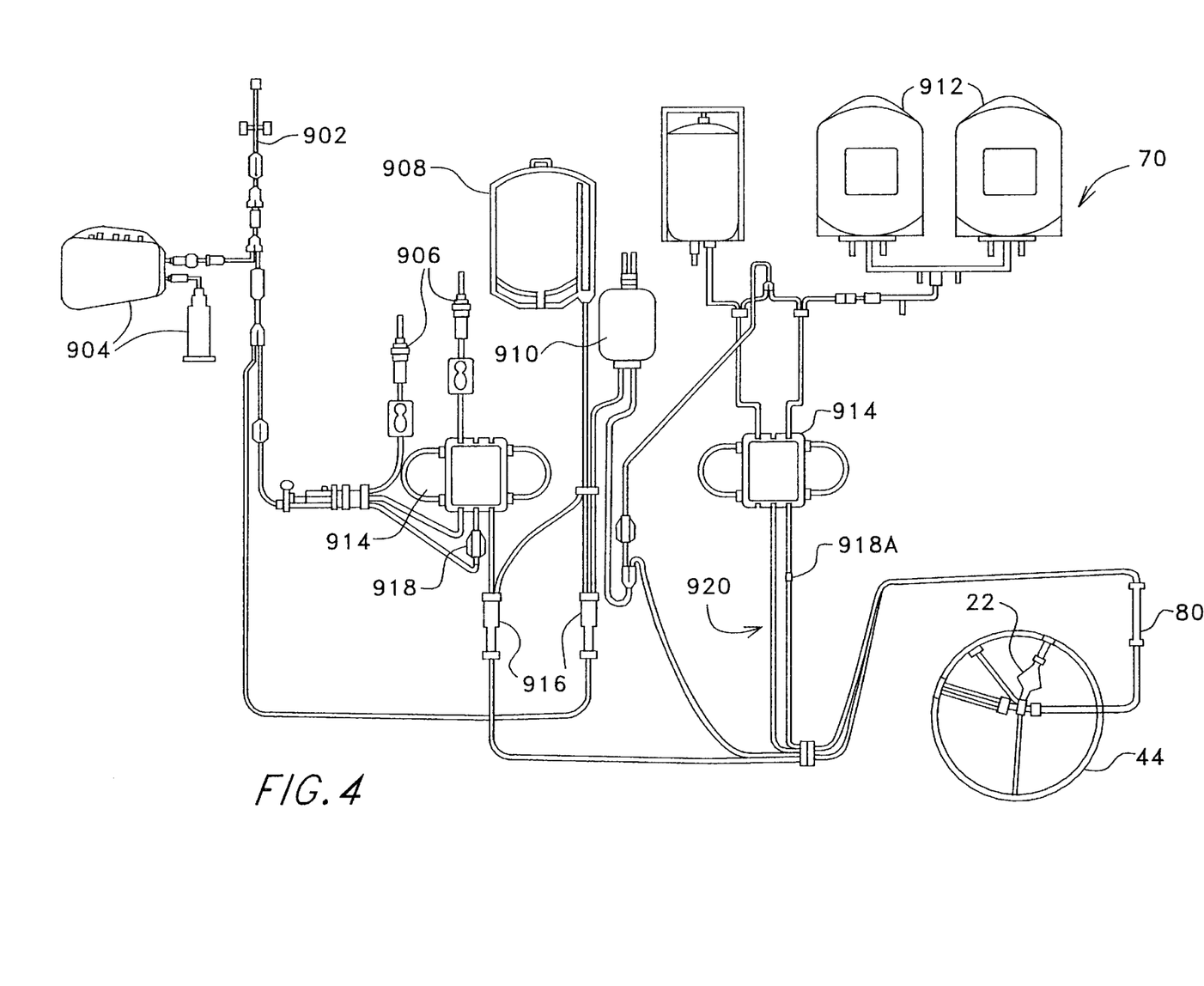
FIG. 4 is a schematic diagram illustrating a tubing set in accordance with the present invention.

FIG. 4 is a more complete view of the tubing set 70 or disposable. The tubing set 70 may further include a plurality of additional elements for collecting blood components including, but not limited to one or more donor access lines 902, sample devices 904, spikes 906, filled solution bags (not shown) for the addition of fluids to the tubing set 70, waste bags 908, accumulator bags 910, blood component bags 912, pump cartridges 914 for interfitting with various fluid pumps such as the pump 36, air chambers 916, monitoring device interfaces 918, interconnecting tubing and fittings 920, and various miscellaneous elements and accessories. In the preferred embodiment the blood component bags 912 are used to collect platelets, specifically at least one collection of hyperconcentrate platelets.

In operation, as shown in FIG. 3, a separation chamber 46 is positioned within a flow passage of the channel 44. During the centrifugation process particles initially separate within the separation chamber 46 according to density and/or sedimentation velocity in response to centrifugal force. The separation chamber 46 includes a ridge 48 positioned on an outer wall of the passageway 14 for deforming a portion of the chamber 46 to create a dam 50 within the chamber 46. Alternatively, the dam 50 may be a permanent structure mounted within the flow passage of the channel 44. Although only a single separation chamber 46 and dam 50 are depicted in the figures, the flow passage may have multiple separation chambers or dams depending upon desired use.

When channel 44 is positioned in passageway 14, a collect well 54 forms in channel 44 adjacent dam 50. A tubing segment 42 connecting an outlet 56 of the well 54 to the inlet 28 of the fluid chamber 22 allows for separated substances in the collect well 54 to be conveyed to the fluid chamber 22. Although the preferred embodiment includes a tubing segment 42, any fluid coupling may be used between the separation chamber 46 and fluid chamber 22. For example, the inlet 28 of fluid chamber 22 may be directly connected to channel 44.

The procedure and method for collecting hyperconcentrated platelets will now be more fully described with reference to the apparatus described above.

The method of separating and collecting hyperconcentrated platelets is discussed with particular reference to FIG. 3. Although the invention is described in connection with a blood component separation process, it should be understood that the invention in its broadest sense is not so limited. The invention may be used to separate a number of different particles. In addition the invention is applicable to both double needle and single needle blood purification or filtration applications. For example, the invention of the present application may be practiced with the SINGLE NEEDLE APHERESIS CONTROL of U.S. Pat. No. 5,437,624 incorporated herein by reference. Also, the invention is described with particular reference to platelets. It is understood, however, that the invention may be practiced to collect other hyperconcentrates.

For blood component separation, the fluid chamber 22 preferably is initially primed with a low density fluid medium, such as air, saline solution, or plasma, having a density less than or equal to the density of liquid plasma. This priming fluid allows for efficient establishment of a saturated fluidized bed of platelets within the fluid chamber 22. When a saline solution is used, this liquid enters the channel 44 through supply line 78. The saline then flows into the outlet 56 and through the chamber 22 when controller 40 activates collect pump 36. Controller 40 also initiates operation of the motor 16 to rotate the centrifuge rotor 12 and fluid chamber 22 in the direction of arrow "B" in FIG. 3. During rotation, twisting of fluid lines 72, 74, 76, 78 and outflow tubing 38 connected to the centrifuge rotor 12 and fluid chamber 22 is prevented by a sealless one-omega/two-omega tubing connection as is known in the art and described in U.S. Pat. No. 4,425,112.

After the apparatus is primed, and as the centrifuge rotates, whole blood or blood components are introduced through supply line 78 into the semi-rigid channel 44. When whole blood is used, the whole blood can be added to the semi-rigid channel 44 by transferring the blood directly from a donor through supply line 78. In the alternative, the blood may be transferred from a container, such as a blood bag, to supply line 78.

The blood within the channel 44 is subjected to a centrifugal force as the centrifuge rotor 12 continues to rotate in the direction of arrow "B" in FIG. 3. This centrifugal force acts in a radial direction away from the axis of rotation 13 of the rotor 12 as indicated by arrow "C" in FIG. 3.

The blood components undergo an initial separation within the channel 44. The components of whole blood stratify in order of decreasing density as follows: 1. red blood cells, 2. white blood cells, 3. platelets, and 4. plasma. The controller 40 regulates the rotational speed of the centrifuge rotor 12 to ensure that this particle stratification takes place. The blood particles form a buffy coat layer 58 and an outer layer 60 along an outer wall surface of the channel 44 within the separation chamber 46. The outer layer 60 includes particles having a density greater than the density of the particles in the buffy coat layer 58. Typically, the outer layer 60 includes red blood cells and white blood cells, while the buffy coat layer 58 includes platelets and white blood cells.

Plasma, the least dense blood component, flows within the channel 44 along the top surface of the buffy coat layer 58. When the height of the buffy coat layer 58 approaches the top of dam 50, the flowing plasma washes the platelets and some white blood cells of the buffy layer 58 over the dam 50. After these particles are washed over the dam 50, they enter the collect well 54. Some of the platelets may also flow past the collect well 54 and then reverse direction to settle back into the collect well 54, as described in a U.S. patent application Ser. No. 08/422,598, now U.S. Pat. No. 5,704,889, entitled SPILLOVER COLLECTION OF SPARSE COMPONENTS SUCH AS MONONUCLEAR COMPONENTS OF WHOLE BLOOD, filed Apr. 14, 1995, the disclosure of which is incorporated herein by reference.

The white blood cells and red blood cells within the outer layer 60 are removed through outlet line 74, while platelet poor plasma is removed through outlet line 72. The controller 40 may control optional pumps (not shown) connected to lines 72, 74, or 76 to remove these blood components, as is known in the art. After the red blood cells, white blood cells, and plasma are thus removed, they are collected and recombined with other blood components or further separated. Alternately, these removed blood components may be reinfused into a donor.

Plasma carries platelets and white blood cells from the collect well 54 into the fluid chamber 22, filled with the priming fluid, so that a saturated fluidized particle bed may be formed. The controller 40 maintains the rotational speed of the rotor 12 within a predetermined rotational speed range to facilitate formation of this saturated fluidized bed. In addition, the controller 40 regulates the collect pump 36 as more fully described below to convey plasma, platelets, and white blood cells at a predetermined flow rate through the tubing segment 42 and into inlet 28 of the fluid chamber 22. These flowing blood components displace the priming fluid from the fluid chamber 22.

The controller 40 regulates the rotational speed of the rotor 12 and the flow rate of the pump 36 to collect platelets and white blood cells in the fluid chamber 22 during a separation phase. As plasma flows through the fluid chamber 22, the flow velocity of the plasma decreases as the plasma flow approaches the maximum cross section area 33. This flow reaches a minimum velocity at this maximum section area 33. Because the rotating centrifuge rotor 12 creates a sufficient gravitational field in the fluid chamber 22, the platelets accumulate near the maximum cross-sectional area 33 rather than flowing from the fluid chamber 22 with the plasma. The white blood cells accumulate somewhat below the maximum cross section area 33. However, density inversion tends to mix these particles slightly during this initial establishment of the saturated fluidized particle bed.

Preferably, the rotational speed and flow rate are controlled so that very few platelets and white blood cells flow from the fluid chamber 22 during formation of the saturated fluidized particle bed during the separation phase. That is the platelets and white blood cells continue to accumulate in the fluid chamber 22 while plasma flows through the fluid chamber 22. Eventually the platelet bed becomes a saturated fluidized particle bed within the fluid chamber 22. The saturated fluidized particle bed substantially obstructs or prevents white blood cells, from passing through the fluid chamber 22. Plasma flowing into the fluid chamber 22 passes through the platelet bed both before and after the platelet saturation point.

The saturated bed of platelets occupies a varying volume in the fluid chamber 22 near the maximum cross sectional area 33, depending on the flow rate and centrifugal field. The number of platelets in the saturated bed depends on a number of factors, such as the flow rate into the fluid chamber 22, the volume of the fluid chamber 22 and rotational speed. If these variables remain constant, the number of platelets in the saturated fluidized bed remains substantially constant. When the flow rate of blood components into the fluid chamber 22 changes, the bed self adjusts to maintain itself by either releasing excess platelets or accepting additional platelets flowing into the fluid chamber 22. For example, in the instant invention, when the plasma flow rate into the fluid chamber 22 is selected to be the 1–3 mL/min rate as more fully described below, the flow rate allows platelets to remain in a saturated bed of sufficient volume to form a hyperconcentrate when collected. The bed reestablishes itself in the saturated condition at the selected flow rate. Fewer platelets are released from the fluid chamber at the low flow rate as compared to a higher flow rate and the saturated bed of platelets occupies a larger volume in the fluid chamber than a bed established at a higher flow rate. Therefore, the concentration of platelets in the bed is higher due to the decreased release of bed platelets.

Although the bed is saturated with platelets, a small number of white blood cells may be interspersed in the platelet bed. These white blood cells, however will tend to "fall" or settle out of the platelet bed toward inlet 28. Most white blood cells generally collect within the fluid chamber 22 between the saturated platelet bed and the inlet 28, as described in copending patent application Ser. No. 08/423,578, now U.S. Pat. No. 5,674,173.

The saturated fluidized bed of platelet particles functions as a filter or barrier to white blood cells flowing into the fluid chamber 22. When blood components flow into the fluid chamber 22, plasma freely passes through the bed. However, the saturated fluidized platelet bed creates a substantial barrier to white blood cells entering the fluid chamber 22 and retains these white blood cells within the fluid chamber 22. Thus, the bed effectively filters white blood cells from the blood components continuously entering the fluid chamber 22, while allowing plasma and platelets released from the saturated bed to exit the chamber 22. This replenishment and release of platelets is referred to as the bed's self-selecting quality. Substantially all of these filtered white blood cells accumulate within the fluid chamber 22 between the saturated fluidized platelet bed and the inlet 28.

To collect hyperconcentrate platelets the centrifuge procedure is allowed to run at the machine default flow rate between 2 mL/min to 8 mL/min until approximately 500 mL of blood has been processed by the centrifuge. This is called the initial phase. Platelets are defined as being of regular concentration if the number of platelets are <$2.1 \times 10^6/\mu L$. In one preferred embodiment the controller then varies the speed of the collect pump 36 to select the flow rate of fluid into the fluid chamber 22 to achieve the desired hyperconcentrate platelet product. The selected flow rate is between 1–3 mL/min although this can be varied depending on the mechanics of the pump. The collection procedure continues at this rate until the fluid chamber is saturated with a saturated bed of platelets sufficient to produce a hperconcentrate collection product in the manner described above.

A collect concentrate monitor or flow monitor may be provided at monitoring device interface 918A in FIG. 4 to detect the saturated state of the fluid chamber. The collect concentrate monitor also may be located on collect line 38 (not shown). The collect concentrate monitor can be of the type described in U.S. Pat. No. 4,810,090. The collect concentrate monitor detects the presence or absence in the collect line 38 of platelets from the fluid chamber and based on the release of platelets monitors the saturated state of the bed. Thus the monitor can determine when the bed begins to form and the collect flow rate should be varied to form the desired saturated bed. Similarly the monitor can determine when the bed reaches the saturated state and starts to release platelets. The monitor provides its output to the controller to vary the collect flow rate through the operation of the pump. Alternatively the monitor can provide its output to the controller wherein the controller instructs the operator through a user interface. The operator can then vary the flow rate as instructed by the system.

The apparatus and method of the invention separate substantially all of the white blood cells from the platelets and plasma flowing through the fluid chamber 22 and concentrate the majority of the platelets in the fluid chamber to provide a leukopoor hyperconcentrate platelet product. The barrier to white blood cells is created, at least in part, because white blood cells have a size and sedimentation velocity greater than that of the platelets forming the saturated fluidized particle bed. Therefore, particles of similar densities are separated according to different sizes or sedimentation velocities.

Because the initial separation at dam 50 and the saturated fluidized bed remove a majority of the red blood cells and white blood cells, the fluid exiting the fluid chamber 22 consists mainly of plasma and some platelets.

At the end of the blood component separation phase in the fluid chamber, platelets in the saturated fluidized bed are harvested to recover a substantial number of platelets from the fluid chamber 22. During bed harvest or the collection phase, the controller 40 allows the flow rate to return to the default rate of from 2–8 mL/min (8 mL/min preferred) and/or decreases the centrifuge rotor 12 speed to release platelets from the bed to remove the accumulated platelets from the chamber. The return to the default rate is done gradually at a rate increase of approximately 0.5 mL/min per minute. This allows the fluid chamber to be gently purged of platelets. The harvesting continues until substantially all of the platelets are removed, and just before an unacceptable number of white blood cells begin to flow from the fluid chamber 22. Preferably the flow rate is gradually increased to 8 mL/min as described above to harvest the platelets from the saturated fluidized bed.

As noted above, the saturated bed can be monitored by a collect concentration monitor in the outlet line to detect the release of any platelets from the saturated bed. Release of platelets indicates the steady state or saturated condition of the bed and signifies that collection can begin. Alternatively, the outlet line can be visually observed. Similarly, the collect concentration monitor can detect white blood cells to determine when an unacceptable number are released or a visual observation can be made.

The harvested platelets are collected in a volume of 50–60 mL. The hyperconcentrated platelets can be collected in the platelet collect bags available with the single or dual needle regular or extended life platelet sets for the COBE® Spectra™ available from the assignee of the existing invention. The typical 1 liter bags can be folded or clipped to reduce the volume by approximately 50%, an amount necessary to accommodate the platelets and to provide as uniform as possible exposure of the platelet concentrate to the gas exchange surface area of the bag. Although it is typical for hyperconcentrated platelets to be transfused within 36 hours it is also possible to store the bags of platelets on to and fro agitators at approximately 22° C. for up to 11 days. It is understood that other known methods of storage and other storage conditions can be used. In addition, the remainder of the contents of the fluid chamber 22, having a high concentration of white blood cells, can be separately collected for later use or recombined with the blood components removed from channel 44 for return to a donor.

Although the invention has been described with respect to a controller varying the speed of the pump based on monitor input it is also possible for an operator to make manual adjustment of the flow rate from the desired yield of platelets or concentration of platelet per mL. The desired collect pump flow rate as described above determines the speed of the pump.

The desired yield or platelet concentrate is related to the target collect volume as follows.

$$\frac{\text{yield of platelets}}{\text{concentration of platelets}} = \text{target collect volume}$$

Table 1 determines the target collect flow rate from the desired yield or concentration of platelets. The table was derived for a 100 minute procedure in accordance with $$\text{target yield of platelets} = 6.75 \times 10^{10} + \frac{1.88 \times 10^{11}}{\text{target flow rate}}.$$

For procedures of other time periods $$\text{target yield of platelets} = k + \frac{K}{\text{target flow rates}}$$

where k and K are constants. PLT in Table 1 is the platelet count.

TABLE 1

Target Collect Flow Rate

| Target Yield 60 mL ($\times 10^{11}$) | Target [PLT] ($\times 10^9$/mL) | Target Collect Flow Rate (mL/min) |
|---|---|---|
| $2.6 \times 10^{11}$ | $4.3 \times 10^9$ | 1.0 |
| $1.9 \times 10^{11}$ | $3.2 \times 10^9$ | 1.5 |
| $1.6 \times 10^{11}$ | $2.7 \times 10^9$ | 2.0 |
| $1.4 \times 10^{11}$ | $2.3 \times 10^9$ | 2.5 |
| $1.3 \times 10^{11}$ | $2.2 \times 10^9$ | 3.0 |
| $1.2 \times 10^{11}$ | $2.0 \times 10^9$ | 3.5 |

To determine the new target collect volume to be inputted by the operator to achieve the collect pump flow rate the operator follows the following procedure. After approximately the selected volume, which may preferably be 500 mL of volume, has been inputted to the apheresis system for processing, the time for such processing and the volume collected are recorded. From the time parameter for inputting 500 mL the change in volume can be determined in accordance with the following chart directed to the change in volume for a 100 minute procedure.

TABLE 2

DELTA VOLUME
(100 minute procedure)

| Time | Target Collect Flow Rate (mL/min) | | | | | |
|---|---|---|---|---|---|---|
| (t) | 1.0 | 1.5 | 2.0 | 2.5 | 3.0 | 3.5 |
| 9 | 124 | 166 | 208 | 250 | 292 | 334 |
| 10 | 123 | 165 | 206 | 248 | 289 | 331 |
| 11 | 122 | 163 | 204 | 245 | 286 | 327 |
| 12 | 121 | 162 | 202 | 243 | 283 | 324 |
| 13 | 120 | 160 | 200 | 240 | 280 | 320 |
| 14 | 119 | 159 | 198 | 238 | 277 | 317 |
| 15 | 118 | 157 | 196 | 235 | 274 | 313 |

The delta volume of the chart was derived from $\Delta$ volume= (93-t)×target flow rate+40 for a 100 minute procedure. For procedures of other lengths $\Delta$ Vol=(R-t)×flow rate+r where R and r are constants. The target collect volume can be calculated as follows:

$V_{collect}$+Delta V=New Target Collect Volume

Figure 5:
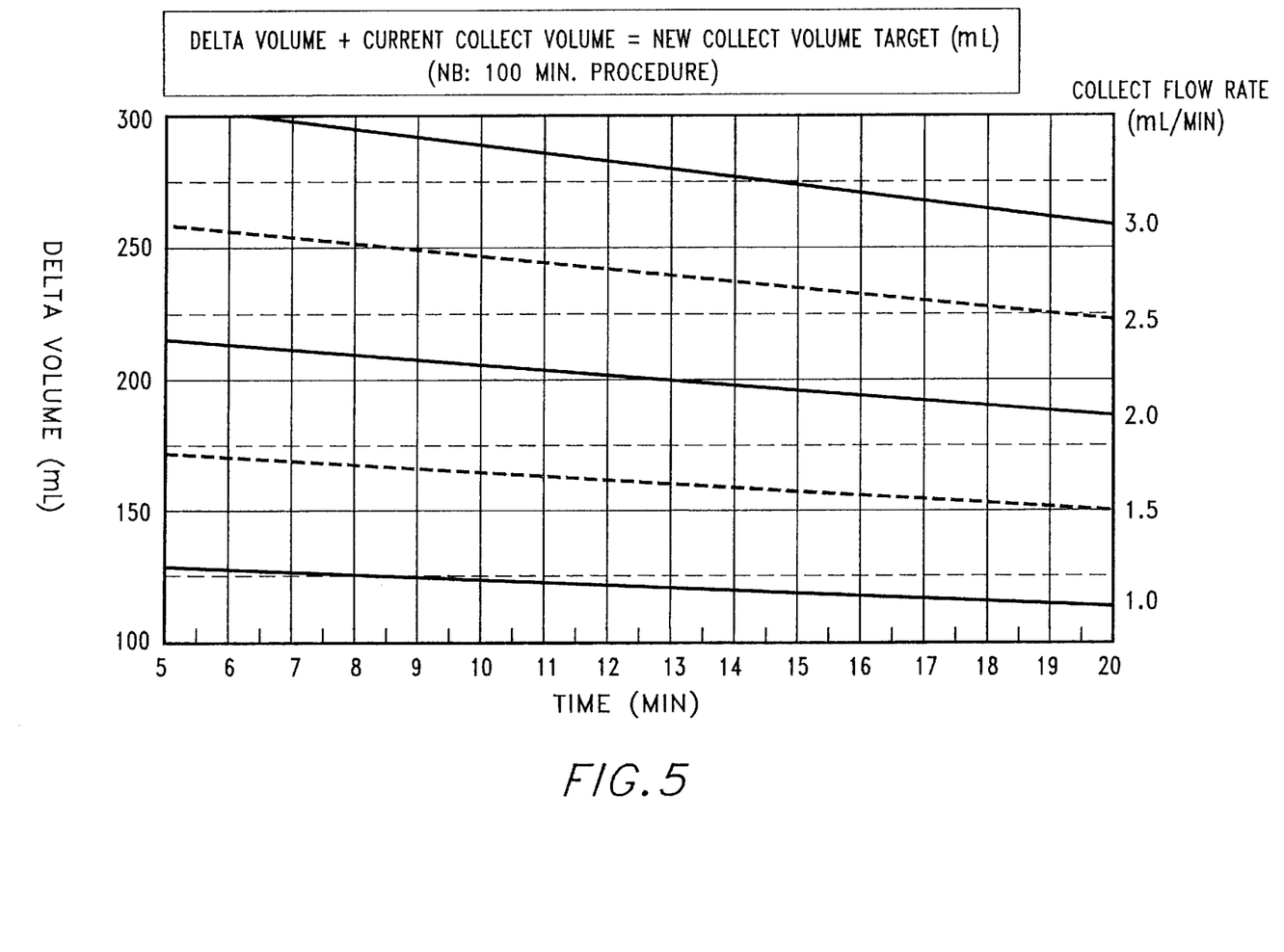
FIG. 5 is a graph for determining a collect volume target.

The $V_{collect}$ is the volume collected after collecting the selected amount or preferably the 500 mL. It is an instantaneous volume at that point in the procedure. The operator then inputs the new target collect volume to achieve the desired collect pump flow rate required by the procedure. A graph, such as that shown in FIG. 5, can also be used to determine the new collect volume target from the delta volume.

The above procedure may be necessary on some apheresis apparatus because the operator may not be able to directly input the desired flow rate but can input the target collect volume. It is understood that the operator can also directly vary or set the flow rate if allowed by the particular apheresis system. Alternatively the operator can also use the above relationships to input the desired yield or concentration of platelets to vary the flow rate. That is, the requisite flow rate can be determined from the particular concentration desired.

EXAMPLE

For a desired platelet yield of $1.9 \times 10^{11}$ the corresponding target collect flow rate is 1.5 mL/min. For a time of 11 minutes and a collect volume of 20 the corresponding $\Delta$ volume is 163 mL. $V_{collect}$+Delta Volume=New Collect Volume Target or 20+163=183.

It is also possible to collect both hyperconcentrated and regular concentration platelets from the same donor during the same procedure and such a feature can be input by the operator. After the collection of the 60 mL of hyperconcentrated platelets the hyperconcentrate product collection bag is clamped. Another second bag is then unclamped to receive product. The collect volume target is changed resulting in the associated collect flow rate changing to the initial default settings of 2 to 8 mL/min to collect a regular concentration platelet product.

Figure 6:
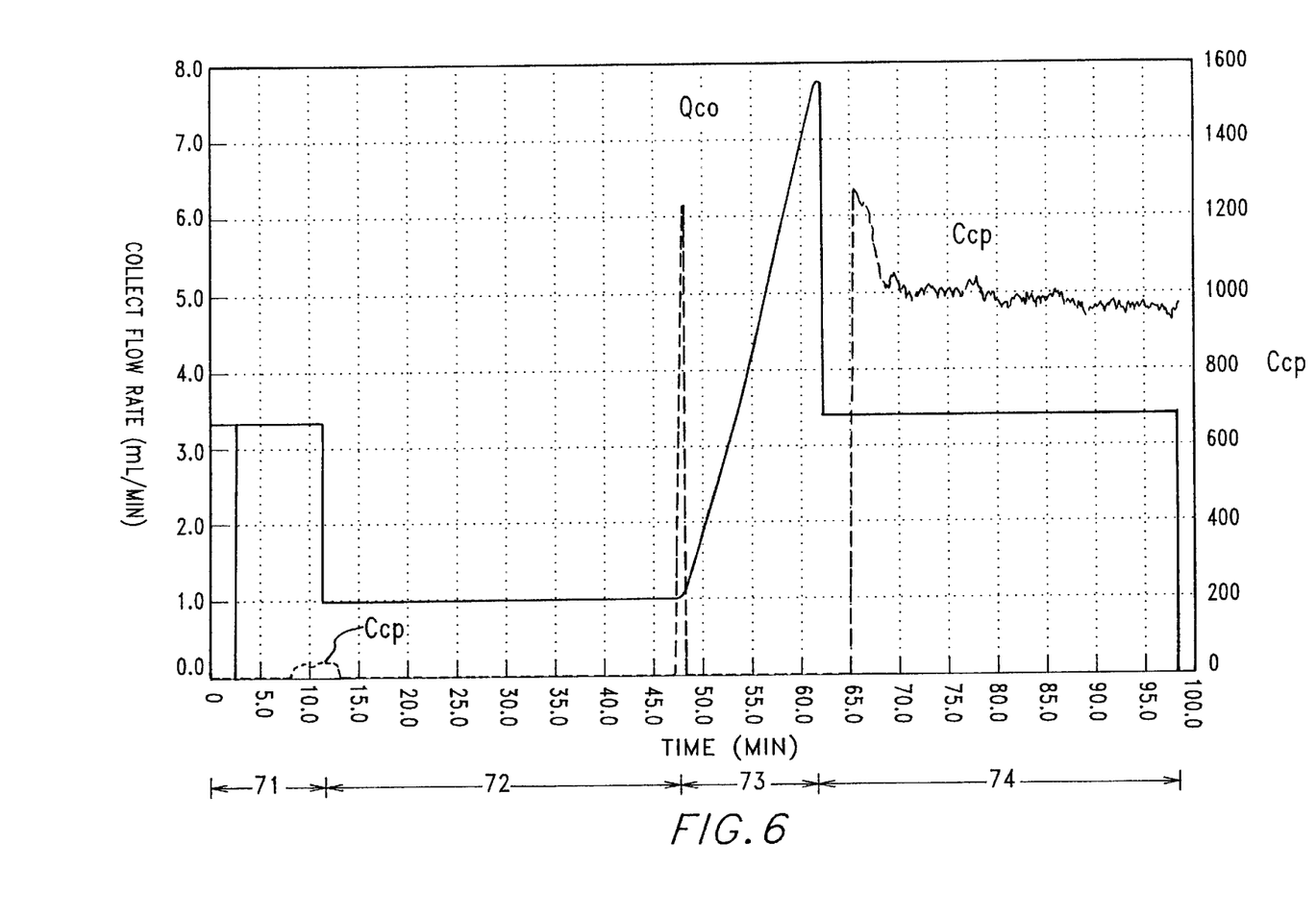
FIG. 6 is a graph of the hyperconcentrate procedure time profile of collect flow rate.

FIG. 6 is a procedure time profile of the collect flow rate identified as Qco The initial phase of the hyperconcentrate procedure is shown at 71 and the apheresis system during this phase is running at normal conditions. The flow rate is then varied or dropped to 1 mL/min for the separation phase 72 wherein the saturated bed of requisite volume is formed. The collection phase is shown at 73 and the graph illustrates the progressive increase of Qco to gently purge the fluid chamber. The flow rate then sharply drops after collection of the hyperconcentrate and regular concentration platelets are collected at approximately 3 mL/min flow rate, (shown at 74). It is noted that the flow rate for the collection of the hyperconcentrate product gradually varies over time during the collection phase 73. This provides a gentle purge of the fluid chamber. The flow rate for collection of the regular concentration product is substantially constant during the regular concentration collection.

In FIG. 6 Ccp is the platelet readout of the collect concentrate monitor 918A. With the more automatic procedure described above the detection of the requisite platelets by the collect concentrate monitor initiates the separation phase. The sudden drop in Ccp when the collection phase of the hyperconcentrate was initiated (approximately 45 minutes) is because the collect concentration monitor was removed from the outlet line during the collection of the hyperconcentrate product.

Although the above procedures have been described with respect to a single collection of hyperconcentrated platelets to complete the collection volume, it is understood that the fluid chamber could also be systematically and sequentially purged. That is, less than the final volume of the collection could be purged from the chamber, with the purging or collection process being repeated during the collection phase. For example, after a saturated bed of platelets has formed, the fluid chamber could be purged of 20 mL. The process could be repeated with 20 mL being removed each repetition to achieve the final desired collection volume. That is, the fluid chamber could be purged a number of times to achieve the total transfusion volume. It is also understood that the final collection volume can be varied from 50–60 mL and that the total collection volume of a single transfusion could be greater or less.

The above procedures yielded a hyperconcentrated platelet capable of storage. Platelet yield and residual white blood cell counts of the hyperconcentrated product were evaluated over the period of storage.

Twelve procedures were completed for the collection of regular and hyperconcentrated platelets following the procedures outlined above. The results are summarized in Table 3. PIR #1 is the time for the collection phase. The time to PIR #1 is the time from the beginning of the procedure to the start of the collection phase.

TABLE 3

Summary Results

| Number of Runs | collect flow rate (mL/min) | | | | | |
|---|---|---|---|---|---|---|
| | 1 n = 6 | | 2 n = 3 | | 3 n = 3 | |
| | mean | sd | mean | sd | mean | sd |
| time to PIR #1 | 45 | 6.1 | 35 | 3.6 | 23 | 2.5 |
| Regular | | | | | | |
| [PLT] [$x10^6$/uL] | 1.13 | 0.30 | 1.20 | 0.21 | 1.78 | 0.13 |
| plt # $x10^{11}$ | 3.12 | 0.88 | 4.15 | 1.63 | 5.37 | 0.50 |
| volume, bag 1 | 285 | 31 | 339 | 104 | 301 | 21 |
| Total WBC (median) | $6.9 \times 10^5$ | | 0 | | 0 | |
| Hyperconcentrate | | | | | | |
| [PLT] [$x10^6$/uL] | 4.46 | 0.54 | 3.03 | 0.55 | 2.22 | 0.30 |
| plt # $x10^{11}$ | 2.72 | 0.33 | 1.81 | 0.25 | 1.39 | 0.07 |
| volume (mL) | 61 | 2 | 57 | 2 | 64 | 10 |
| Total WBC (median) | $1.5 \times 10^4$ | | 0 | | 0 | |

All products collected contained less than $1 \times 10^6$ total white blood cells. When the collect flow rate was selected to be <8 mL/min for the collection of the regular concentration of platelets the white blood cell count was further reduced.

Although the above apparatus and method has been used for the separation and the collection of platelets specifically of hyperconcentrated platelets, it is understood that it could be used for the separation and collection of hyperconcentrates of other particles.

It will be apparent to those skilled in the art that various modification can be made to the structure and methodology of the present invention without departing from its spirit or scope. It is intended that the present invention cover modifications of this invention that they come within the scope of the following claims and their equivalents.

What is claimed is:

1. A method of collecting a hyperconcentrated platelet product the method comprising the steps of
   providing a fluid chamber having an inlet and an outlet;
   flowing a fluid containing platelets and other particles at a flow rate into the fluid chamber;
   selecting the flow rate of the fluid containing platelets and other particles to be sufficiently low to retain the majority of the platelets in the fluid chamber;
   forming with the retained platelets a saturated fluidized bed of platelets in the fluid chamber;
   maintaining the other particles between the inlet of the fluid chamber and the saturated bed while passing the fluid through the saturated bed to the outlet of the fluid chamber;
   collecting the platelets in the saturated bed without collecting the majority of the other particles to form a hyperconcentrated other particle reduced platelet product.

2. The method of claim 1 wherein the other particles are primarily white blood cells.

3. The method of claim 1 wherein the flow rate is selected to be approximately 1–3 mL/min of fluid.

4. The method of claim 3 further comprising the step of maintaining the flow rate at 1–3 mL/min while forming with the retained platelets the saturated fluidized bed of particles.

5. The method of claim 1 further comprising the steps of
   monitoring the outlet of the fluid chamber to determine when the saturated bed has reached its maximum steady state and platelets are being released from the bed; and
   increasing the flow rate to collect the platelets in the saturated bed.

6. The method of claim 1 further comprises the step of increasing the flow rate over time to collect the platelets in the saturated bed.

7. The method of claim 1 further comprising the steps of
   selecting the desired concentration of platelets to be collected;
   determining a target collect volume for the desired concentration of platelets; and
   the step of selecting the flow rate of the fluid further comprises
   altering the target collect volume to select the flow rate of the fluid.

8. The method of claim 1 wherein the step of flowing the fluid further comprises
   providing a collect pump for flowing the fluid;
   and the step of selecting the flow rate comprises
   controlling the collect pump to select the flow rate.

9. The method of claim 8 wherein the step of controlling the collect pump further comprises providing a controller to adjust the operating speed of the collect pump.

10. The method of claim 1 further comprising the steps of selecting the desired yield of platelets to be collected;
    determining a target collect volume for the desired yield of platelets; and
    the step of selecting the flow rate of the fluid further comprises
    altering the target collect volume to select the flow rate of the fluid.

11. A method of separating platelets from other particles the method comprising the steps of:
    providing a fluid chamber having an inlet and an outlet;
    rotating the fluid chamber about a rotor;
    passing a quantity of fluid having platelets and the other particles at a first flow rate into the inlet of the rotating fluid chamber;
    changing the flow rate of the fluid to a second flow;
    forming, with the platelets in the fluid at the second flow rate, a saturated fluidized bed of platelets within the rotating fluid chamber;
    flowing the fluid through the fluid chamber from the inlet to the outlet while maintaining the bed within the fluid chamber, so that the bed substantially prevents flow of the other particles from the fluid chamber inlet to the fluid chamber outlet while permitting flow of the fluid to the outlet; and
    removing the platelets in the saturated bed from the fluid chamber wherein the platelets in the saturated bed form a hyperconcentrated other particle reduced platelet product.

12. The method of claim 11 wherein the other particles are white blood cells.

13. An apparatus for separating platelets from other particles during a separation phase and collecting separated hyperconcentrated platelets during a collection phase, the apparatus comprising:

a motor;

a centrifuge rotor coupled to the motor for rotation about an axis of rotation;

a fluid chamber connected to the rotor for rotation with the rotor, the fluid chamber having an inlet and an outlet;

means for supplying liquid and platelets and other particles at a flow rate to the inlet of the fluid chamber;

means for controlling the supplying means to vary the flow rate to maintain a saturated fluidized bed of platelets within the fluid chamber and to cause the other particles to be retained in the fluid chamber during the separation phase;

said means for controlling further varying the flow rate to move the platelets in the saturated bed from the fluid chamber without moving the majority of the other particles during the collection phase.

14. The apparatus of claim 13 wherein the means for supplying comprises a pump.

15. The apparatus of claim 14 wherein the pump flows the liquid and platelets and other particles to the inlet of the fluid chamber and flows the liquid from the outlet of the fluid chamber during the separation phase.

16. The apparatus of claim 15 wherein the pump further removes platelets from the fluid chamber during the collection phase.

17. The apparatus of claim 14 wherein the means for controlling comprises a controller for varying the speed of the pump to correspondingly vary the flow rate.

18. The apparatus of claim 17 wherein the controller controls the pump to maintain a flow rate of 1–3 mL/min during the separation phase.

19. The apparatus of claim 17 wherein the controller controls the pump to gradually increase the flow rate during the collection phase.

20. The apparatus of claim 13 wherein the means for controlling comprises a controller.

21. The apparatus of claim 13 wherein the flow rate is increased in the collection phase to approximately 8 mL/min.

22. The apparatus of claim 21 wherein the flow rate is gradually increased during the collection phase at the rate of approximately 0.5 mL/min.

23. The apparatus of claim 13 wherein the means for controlling the supplying means further varies the flow rate to initiate the establishment of the saturated fluidized bed within the fluid chamber during an initial phase.

24. The apparatus of claim 23 wherein the flow rate during the initial phase is greater than the flow rate during the separation phase.

25. The apparatus of claim 23 further comprising a monitor to detect release of platelets from the fluid chamber outlet, the monitor providing input to the means for controlling the supplying means to vary the flow rate depending on the number of platelets detected by the monitor.

26. The apparatus of claim 23 wherein the means for controlling the supplying means changes the flow rate to initiate the separation phase when the number of platelets detected by the monitor increases.

27. The apparatus of claim 13 wherein the means for controlling the supplying means comprises means for determining a desired yield of platelets, and a desired flow rate to achieve the desired yield of platelets.

28. The apparatus of claim 27 further comprising inputting a desired collect volume; and varying the collect volume to vary the desired flow rate to achieve the desired yield of platelets.

29. A method of collecting leuko-reduced platelets comprising providing at a first flow rate a fluid comprising primarily plasma and platelets and some white blood cells to a fluid chamber having a inlet and an outlet;

rotating the fluid chamber about a rotor;

varying the first flow rate to a second lower flow rate to establish a saturated bed of platelets within the rotating fluid chamber;

filtering white blood cells from the fluid with the saturated bed of platelets wherein the white blood cells are retained in the fluid chamber while fluid passes from the inlet through the saturated bed to the outlet;

raising the flow rate from the second flow rate to a third flow rate to release the platelets of the saturated bed from the fluid chamber for collection wherein the platelets collected form a first collection hyperconcentrated leuko-reduced platelet product.

30. The method of claim 29 further comprising monitoring platelets passing out of the outlet of the fluid chamber to determine when to vary the first flow rate to the second flow rate.

31. The method of claim 29 wherein the step of varying the first flow rate to a second flow rate comprises varying the flow rate to 1–3 mL/min.

32. The method of claim 29 wherein the step of raising the second flow rate to the third flow rate comprises raising the flow rate to approximately 8 mL/min.

33. The method of claim 29 wherein the step of raising the second flow rate to the third flow rate comprises gradually raising the flow rate over a period of time.

34. The method of claim 29 further comprising providing a first collection bag having interior surfaces for collection of the first collection product;

folding the collection bag to reduce excess volume of the bag to accommodate the collected amount of the first collection product wherein a substantial portion of the collected amount has exposure to the interior surfaces of the bag; and releasing the platelets forming the saturated bed into the first collection bag.

35. The method of claim 29 further comprising adjusting the flow rate to the first flow rate and maintaining the first flow rate to establish a second saturated bed of platelets with the rotating fluid chamber;

filtering white blood cells from the fluid with the second saturated bed of platelets wherein the white blood cells are retained in the chamber while fluid passes from the inlet through the second saturated bed to the outlet;

collecting the platelets from the second saturated bed to form a second collection leuko-reduced platelet product having a concentration of platelets less than the first collection platelet product.

36. A method of collecting a hyperconcentrated first particle product from a fluid containing the first particles and other particles, the method comprising the steps of providing a fluid chamber having an inlet and an outlet;

flowing the fluid having the first particles and the other particles at a flow rate into the fluid chamber;

selecting the flow rate of the fluid containing first particles and other particles to be sufficiently low to retain the majority of the first particles in the fluid chamber;

forming with the retained first particles a saturated fluidized bed of first particles in the fluid chamber;

maintaining the other particles between the inlet of the fluid chamber and the saturated bed while passing the fluid through the supersaturated bed to the outlet of the fluid chamber;

collecting the first particles in the saturated bed without collecting the majority of the other particles to form a hyperconcentrated other particle reduced platelet product.

37. The method of claim 36 wherein the flow rate is selected to be approximately 1–3 mL/min of fluid.

38. The method of claim 37 wherein the step of collecting further comprises gradually increasing the flow rate over time to remove the first particles from the fluid chamber.

39. The method of claim 36 further comprising the steps of monitoring the outlet of the fluid chamber to determine when the saturated bed has reached its maximum steady state and first particles are being released from the bed; and increasing the flow rate to collect the first particles in the saturated bed.

40. The method of claim 39 wherein said increasing the flow rate step increases the flow rate gradually over time.

41. The method of claim 36 further comprising the steps of selecting the desired concentration of first particles to be collected;

determining a target collect volume for the desired concentration of first particles; and the step of selecting the flow rate of the fluid further comprises altering the target collect volume to select the flow rate of the fluid.

42. The method of claim 36 wherein the step of flowing the fluid further comprises providing a collect pump for flowing the fluid;

and the step of selecting the flow rate comprises controlling the collect pump to select the flow rate.

43. The method of claim 42 wherein the step of controlling the collect pump further comprises providing a controller to adjust the operating speed of the collect pump.

* * * * *